United States Patent [19]
Perry et al.

[11] 3,935,075
[45] Jan. 27, 1976

[54] AUTOMATIC BACTERIAL SPECIMEN STREAKER AND METHOD FOR USING SAME

[75] Inventors: Russell C. Perry, Smithtown; Roy W. Porter, Roslyn Heights, both of N.Y.

[73] Assignee: Diagnostic Research, Inc., Roslyn, N.Y.

[22] Filed: May 13, 1974

[21] Appl. No.: 469,457

[52] U.S. Cl. ............................... 195/127; 195/120
[51] Int. Cl.² ........................................ C12B 1/02
[58] Field of Search ........................... 195/127, 120

[56] References Cited
UNITED STATES PATENTS

| | | | |
|---|---|---|---|
| 3,742,187 | 6/1973 | Folus | 195/120 |
| 3,841,973 | 10/1974 | Wilkins et al. | 195/127 |
| 3,850,754 | 11/1974 | Wilkins et al. | 195/127 |

*Primary Examiner*—Alvin E. Tanenholtz
*Attorney, Agent, or Firm*—Bauer, Amer & King

[57] ABSTRACT

The present invention provides an automatic streaking device for bacterial specimens, which device produces a repetitive, overlapped plurality of figure eight patterns. An electrically conductive loop is displaced in a direction perpendicular to the major axis of the figure eight pattern. Means are provided for non-linearly advancing the loop in a direction perpendicular to the major axis of the figure eight pattern so as to vary the resulting pattern in a predetermined manner. Means are also provided for automatically sterilizing the loop when the series of figure eight movements are terminated. A first motor drives a pair of crank arms having different lengths in order to determine the amplitudes of the figure eight patterns in two mutually perpendicular directions. A second, variable speed, reversible motor is coupled to and drives a carriage that supports the first motor and the crank arms so as to vary the center-to-center spacing between adjacent figure eight patterns.

15 Claims, 10 Drawing Figures

AUTOMATIC BACTERIAL SPECIMEN STREAKER AND METHOD FOR USING SAME

The aforementioned Abstract is neither intended to define the invention of the application which, of course, is measured by the claims, nor is it intended to be limiting as to the scope of the Claims in any way.

BACKGROUND OF THE INVENTION

1. Field of the Invention

This invention relates generally to apparatus for preparing bacterial specimens and more particularly to automated apparatus of this type which prepares the specimens for visual counting, typing and other analysis of the bacterial populations.

2. Description of the Prior Art

One of the many procedures which must be performed in microbiology are plate streaks for isolating microbiological colonies. Distinctly isolated colonies are produced as a result of growth starting with a single cell. The isolated colonies are absolutely necessary for the observance of colony morphology and for the performance of staining and other procedures which are necessary for determining the genus and in many cases, the species, strain, etc. of an unknown organism. Both bacterial and fungus type micro-organisms must be isolated from test samples. In an actual process, a liquid such as isolation broths, blood, urine, etc. or solids such as feces, scrapings, etc. might be used to identify an unknown bacterial. Fungi requires the same type of isolation as bacteria but, unlike the bacterial, the fungi are generally not subjected to additional tests since colony characteristics and microscopic appearance alone are usually adequate for their identification.

Two or three plates are streaked per sample of each test specimen. The streaking process requires approximately 30 seconds per agar plate of a technologist's time. The quality of the streak and therefore the degrees of isolation of the microorganism depends upon the training received by the technologist and the care taken in performing the process.

Problems typically encountered during a streaking process include the use of an improperly cooled inoculating needle following flame sterilization. As a result, the organisms may be destroyed in the streaking process. In addition, contaminants may be introduced by the use of an improperly sterilized inoculating needle. There are also the problems caused by the lack of reproducibility of streaks from one technician to another and the difficulty a technician often encounters in streaking soft agars which are easily cut. An improperly made streak has to be redone before further testing is possible. The detection of a faulty streak may require anywhere from 12 to 48 hours depending upon the rate of growth of the organisms present in the sample.

Several machines have been developed for automatically preparing bacterial specimens. One such machine is disclosed in U.S. Pat. No. 3,778,351 which was granted on Dec. 11, 1973 to Robert J. Rosov. In this patent, means are provided for controlling relative movement of a specimen plate and a dispensing pipette. The volume rate of delivery of the specimen from the pipette to the specimen plate is accurately controlled in order to effect the preparation of the specimen along a pre-determined and reproducible pattern and concentration. Specifically, U.S. Pat. No. 3,778,351 provides a specimen plate having a plurality of laterally elongated grooves that are adapted to contain a bacterial specimen growth base material. The pipette is supported above the specimen plate which includes a frame, a table mounted on the frame for movement in one direction and indexing means on the table for engaging the specimen plate. The indexing means is movable relative to the table in a direction normal to the table movement for aligning each groove selectively with a pipette. As will be explained more fully hereinafter, U.S. Pat. No. 3,778,351 is contrasted from the present invention by virtue of the linear advance of the pipette and by a zig-zag path as opposed to a figure eight path.

SUMMARY OF THE INVENTION

In its broadest aspect, the present invention provides a method and apparatus for producing a repeatedly intersecting figure eight streaking pattern. An electrically conductive loop is driven so as to generate the figure eight pattern having a major dimension in one direction and a minor dimension in a second direction perpendicular to the major dimension. In addition, means are provided for driving the loop in a direction perpendicular to the major dimension so as to form a plurality of continuous, overlapping figure eight patterns. A reversible, variable speed motor is used to determine the center-to-center dimension in a direction parallel to the minor dimension of the overlapped figure eight patterns. As a result, the figure eight patterns cross over each other at several points. At the end of the streaking cycle, means are provided for automatically sterilizing the loop when the loop is returned to its starting position. The loop is then available for the next streaking operation.

Accordingly it is an object of the present invention to provide an improved apparatus for automatically preparing bacterial specimens.

It is another object of the present invention to provide an improved apparatus, as described above, for driving a streaking loop in a figure eight pattern.

It is a further object of the present invention to provide an improved apparatus, as described above, wherein the loop is driven in a figure eight pattern of a continuous nature whereby successive figure eight patterns overlap each other.

Another object of this invention is to provide an improved loop.

Still a different object is to provide an electrically sterilizable loop.

A further object of the present invention is to provide an improved apparatus, as described above, wherein the plurality of figure eight patterns are overlapped in a pre-determined, non-linear relationship.

Still another object of the present invention is to provide an improved method for streaking a bacterial specimen.

These and other objects, features and advantages of the invention will, in part, be pointed out with particularity and will, in part, become obvious from the following more detailed description of the invention, taken in conjunction with the accompanying drawing, which forms an integral part thereof.

BRIEF DESCRIPTION OF THE DRAWING

In the various figures of the drawing, like reference characters designate like parts. In the drawing.

DESCRIPTION OF THE INVENTION

Figure 1:
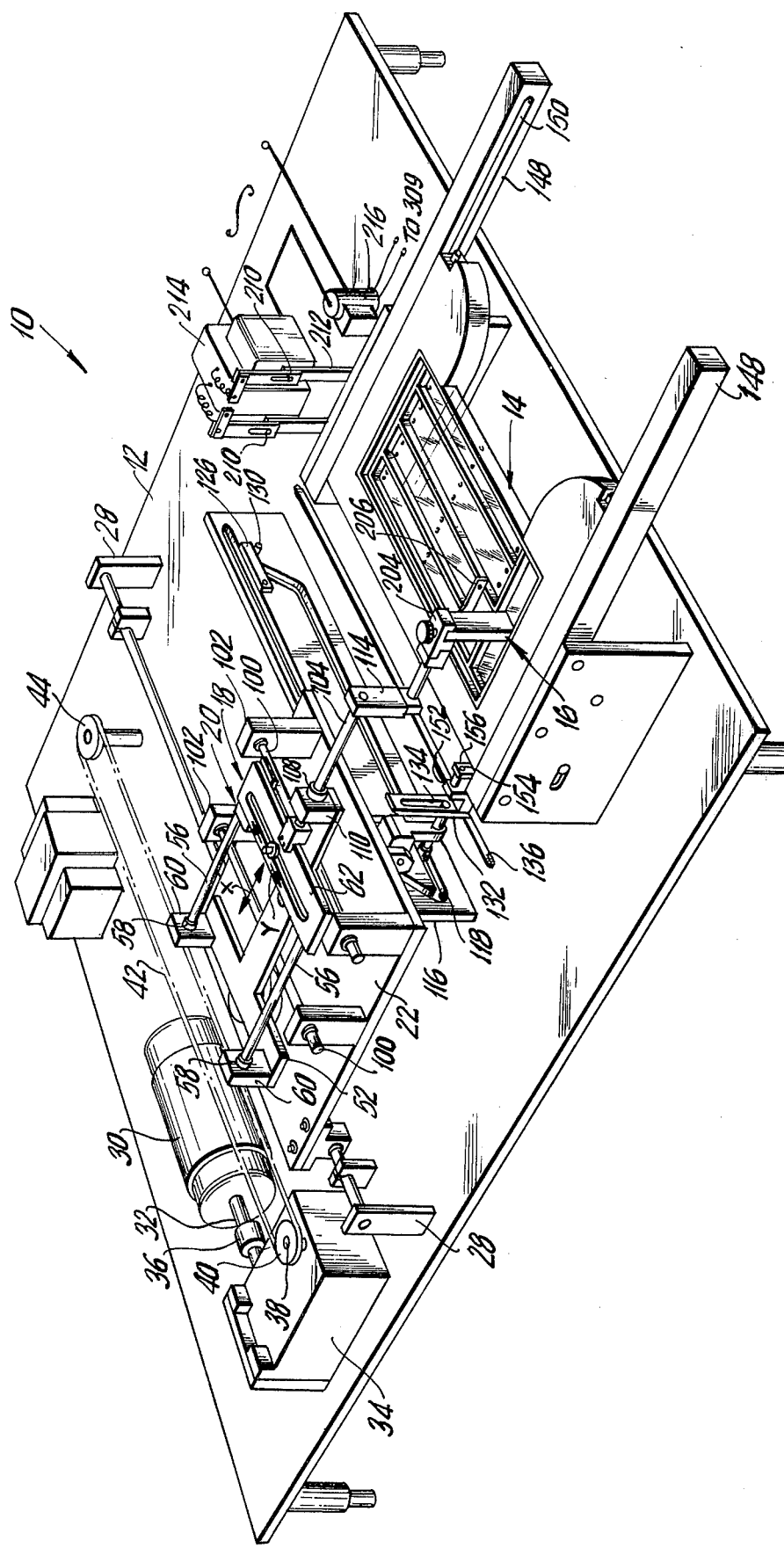
FIG. 1 is a perspective view illustrating one embodiment of the present invention.
Figure 2:
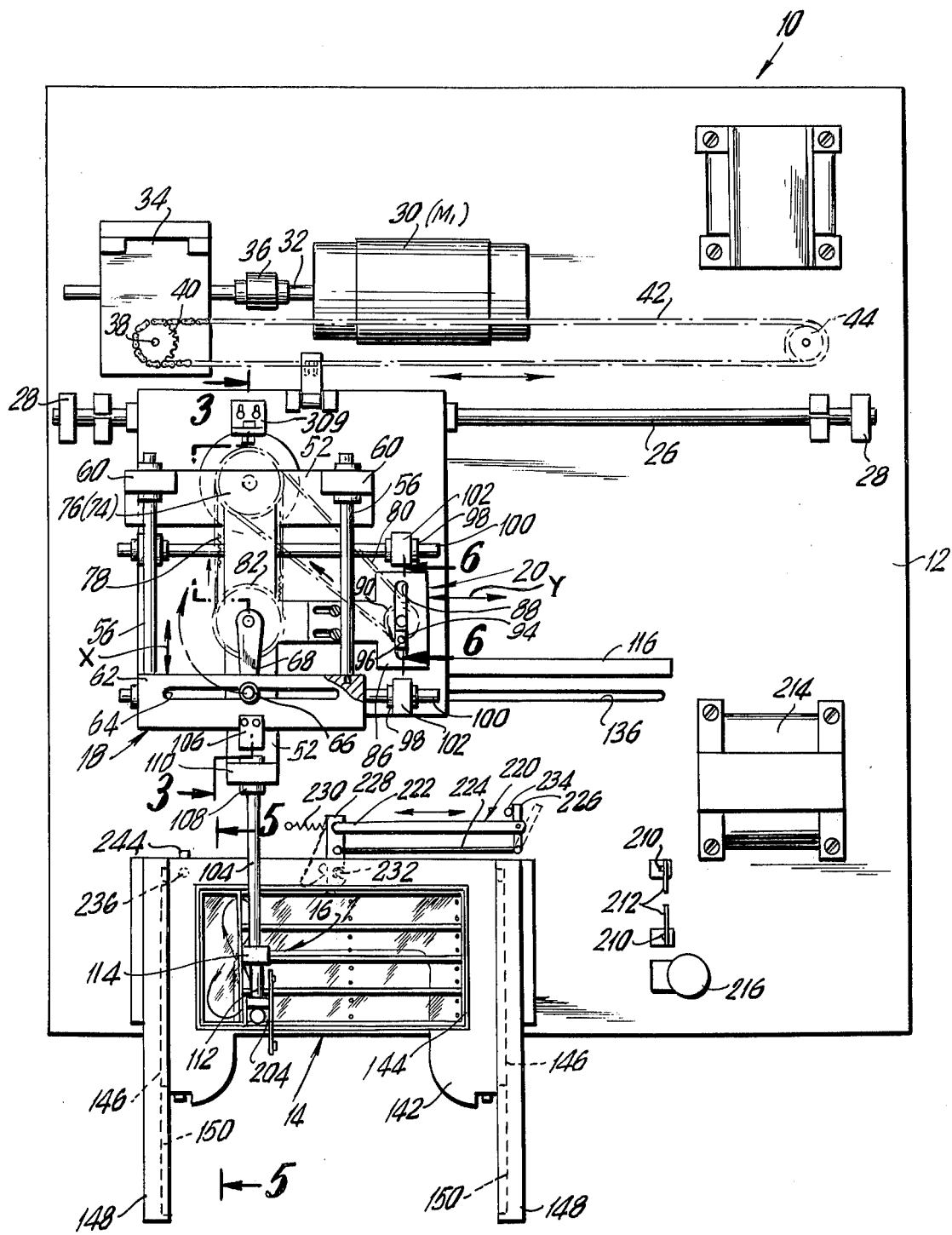
FIG. 2 is a plan view of the apparatus shown in FIG. 1.
Figure 3:
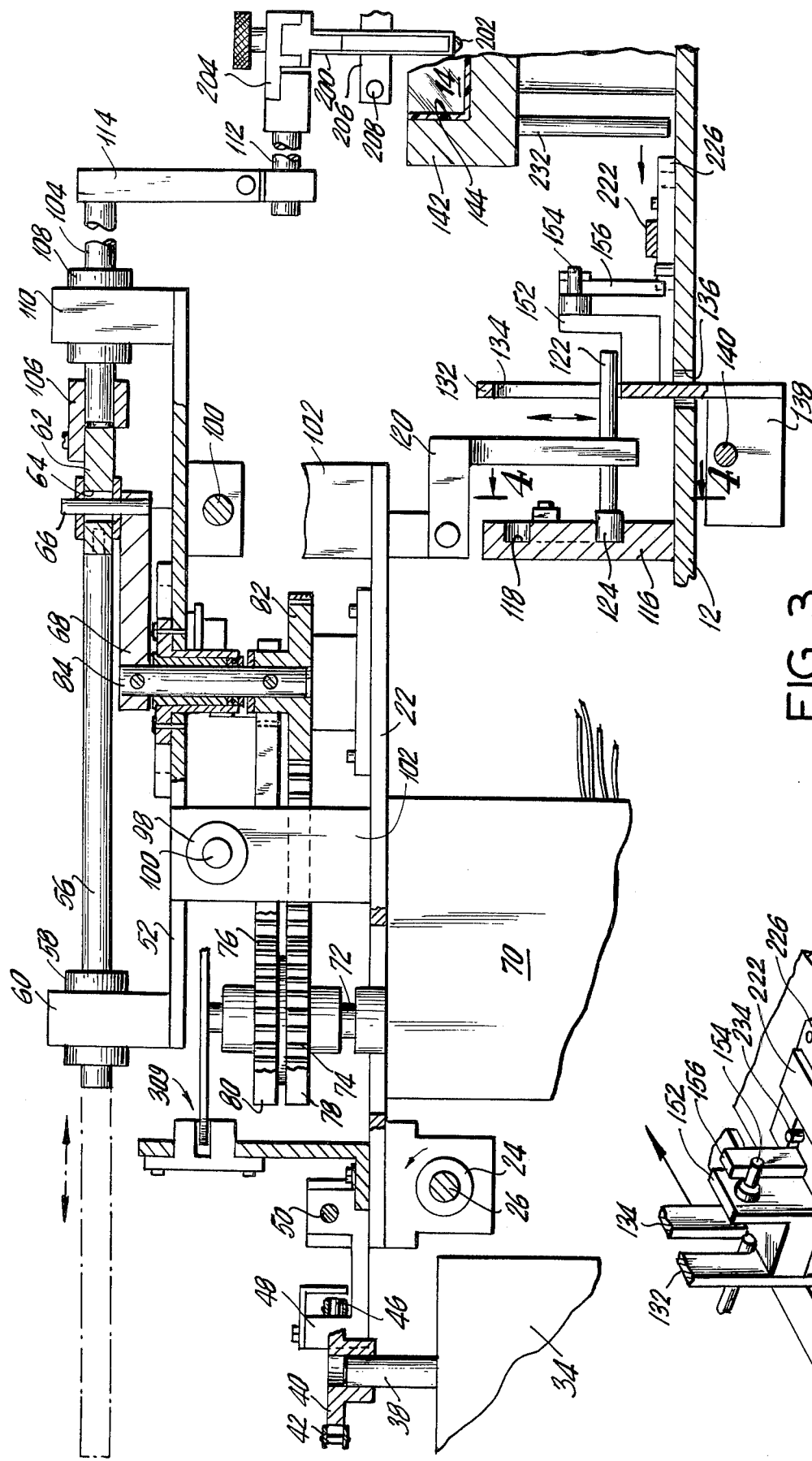
FIG. 3 is a sectional, elevational view, partially in section and partially broken away, taken along line 3—3 as FIG. 2.

Referring now to the drawing, and in particular to FIGS. 1–3 there is shown the structure of an improved bacterial specimen streaker 10 constructed in accordance with the concepts of the present invention. The streaker 10 includes a table 12 on which is mounted, in a manner to be described more fully hereinafter, a multi-compartmented tray 14 which is adapted to contain the inoculated specimen. A loop generally designated by the referenced character 16, is positioned over the tray and is arranged to be driven in a figure eight pattern so as to streak the specimen.

In order to define the figure eight path over which the loop 16 travels, there are provided two crank mechanisms generally designated by the referenced characters 18 and 20 respectively. The crank mechanism 18 generates movement along a major axis designated as X while the crank mechanism 20 generates movement along a substantially perpendicular axis designated as $Y_1$. The combination of movement of the crank mechanisms 18 and 20 define the figure eight patterns shown in FIGS. 7A and 7B.

As shown in FIGS. 2 and 3 for example, the crank mechanisms 18 and 20 are mounted on a carriage 22 which is arranged to move in the $Y_1$ direction. Proximate one edge thereof, the carriage 22 is provided with linear bearing means 24 in which is positioned a shaft 26. Suitable support means 28 are used to mount the shaft on the table 12. A variable speed, reversible motor 30 is also mounted on the table 12 and is used for driving the carriage 22 back and forth in the $Y_1$ direction. The output shaft 32 of the motor 30 is connected to a right angle gear box 34 through a coupling member 36. The output shaft 38 of the gear box 34 is provided with a first sprocket 40 about which is trained an endless chain 42. A second sprocket 44 is also rotatably mounted on the table 12. A pair of pins 46, which are integral with the chain 42, are suitably connected to a bracket 48 which is mounted on the carriage 22. Preferably, the connection between the bracket 48 and the carriage 22 is through a shaft 50 which permits limited relative angular movement therebetween.

The first and second crank assemblies 18 and 20 are defined by a double-T support bracket 52 which is positioned above and secured to the carriage 22 by means of posts 54. The first crank assembly 18 further includes a pair of guide rods 56 which are mounted in linear bearings 58. Support members 60 are used to position the guide rods 56 relative to the bracket 52. A plate 62, which has a slot 64 formed therein, is rigidly coupled to and extends between one end of the guide rods 56 for movement together therewith. A drive pin 66 is positioned within the slot 64 and is driven by a crank arm 68.

A second, constant speed drive motor 70 is mounted on and positioned beneath the carriage 22. The output shaft 72 of the motor 70 supports a pair of coaxial gears 74 and 76. Toothed timing belts 78 and 80 are trained about the gears 74 and 76 respectively. A second pinion 82 is driven by the first belt 78. As shown for example in FIG. 3, a pivot pin 84 is rigidly coupled to the second gear 82 as well as to the first crank arm 68 so that as the second motor 70 is driven, the first crank arm 68 will rotate clockwise (FIG. 2) about the pivot pin 84, and will thereby translate the bracket 62 in the X direction as shown in FIG. 2.

Figure 6:
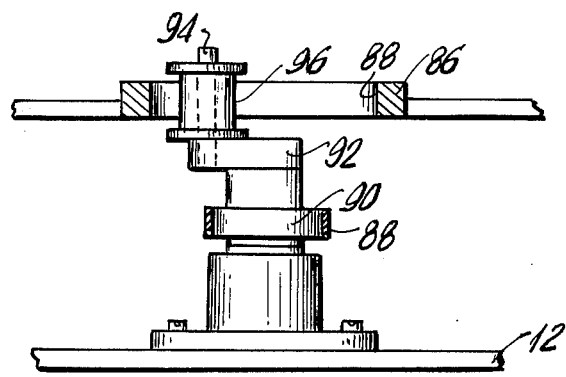
FIG. 6 is a fragmentary elevational view, partially in section taken along line 6—6 of FIG. 2.

The second crank assembly 20 is comprised of a plate 86 having a slot 88 formed therein. The second crank 20 is driven by the timing belt 80, a drive pin 90 which is mounted on the carriage 22 as shown in FIG. 6 and a crank arm 92. A pin 94 extends upwardly from the crank arm 92 and is provided with a rectangular bushing 96 that fits in the slot 88. The plate 86 of the second crank assembly 20 is coupled to linear bearings 98 that ride on guide rods 100. Posts 102 are used for supporting the guide rods 100 on the carriage 22 as shown in FIG. 1 and in FIG. 3. Thus, as the second motor 70 is driven, the second crank arm 92 will rotate in a clockwise direction (FIG. 2) about the axis of the gear 90 to thereby drive the plate 86 in the $Y_1$ direction.

Figure 7A:
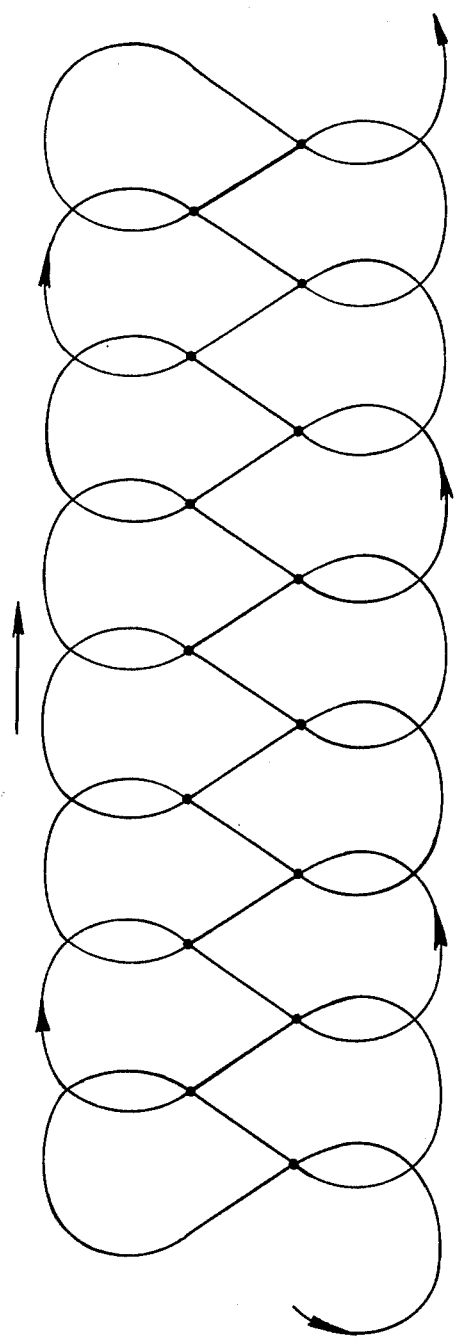
FIGS. 7A and 7B are schematic views illustrating two typical streaking patterns and FIG. 8 is a schematic diagram illustrating the electrical controls for the present invention.
Figure 7B:
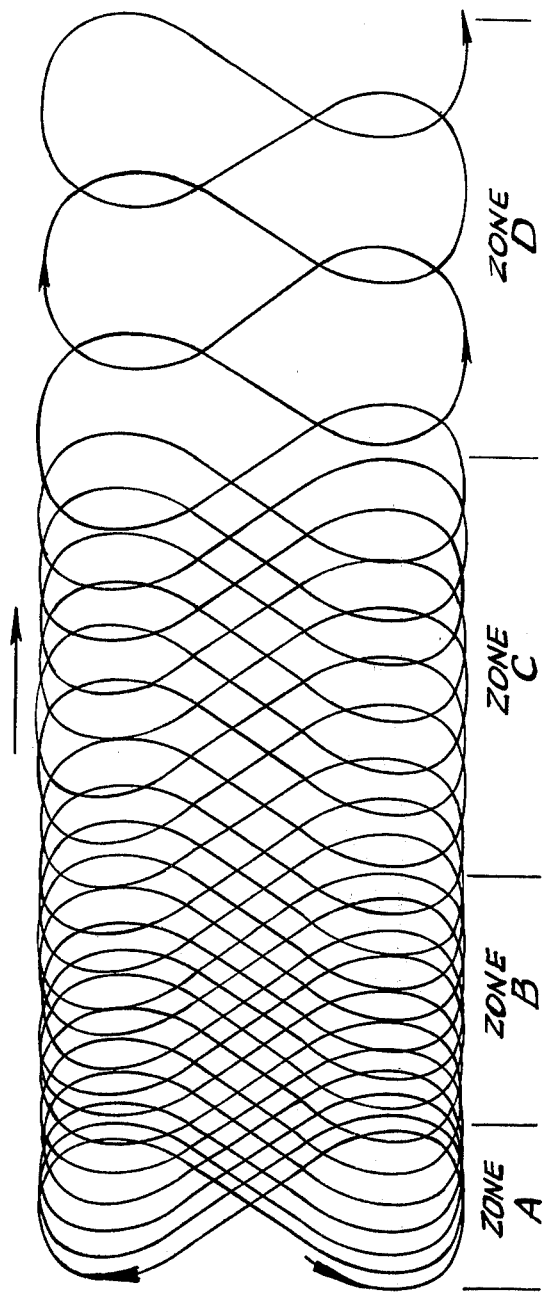

With the motor 70 running, the crank arms 68 and 92 will be simultaneously driven and will thereby generate a figure eight pattern. By way of example, the pulleys driving the crank arms 68 and 92 may have a ratio of 2:1. It will further be appreciated that by the coupling of the carriage 22 to the output of the variable speed motor 30 the figure eight pattern will be repeated such as shown in FIGS. 7A and 7B. As will be explained more fully hereinafter, the center-to-center dimension between adjacent figure eight patterns can be varied.

A shaft 104 is secured to the plate 62 by means of a coupling 106. A linear bearing 108 supports the shaft 104 and is mounted in a post 110 which is secured to the plate 52. The loop 16 is provided with a shaft 112 which is secured to the shaft 104 by means of a bracket 114.

The carriage 22, in addition to moving in the Y direction along the guide rod 26 is also angularly displaced about the axis of the guide rod 26 at the beginning and end of the travel of the loop 16 in the Y direction. This is accomplished by means of a cam plate 116 having a continuous groove 118 formed in one surface thereof. The cam plate 116 is mounted on the plate 12 such as shown in FIG. 3. An arm 120 extends downwardly from the underside of the carriage 22 and carries therewith a shaft 122 on which is mounted a cam follower 124 which engages the cam groove 118. As the carriage 22 moves in the Y direction, and more specifically to the right as shown in FIG. 2, the cam follower 124 will engage the lower track 118a of the cam groove 118. At the end of travel, the cam follower 124 will engage cam track 118b which is inclined upwardly and to the right so as to raise the loop 16. The carriage 22 will then pivot about the axis of the guide rod 26 in a counter clock-wise direction as shown in FIG. 3. The cam follower 124 will then engage the cam track 118c so that the loop 16 will be returned to its starting position but at an elevated location. Proximate the left hand end of the cam track 118, the cam follower 124 will engage the track portion of 118d so that the loop 16 will be lowered and returned to its starting position.

Figure 4:
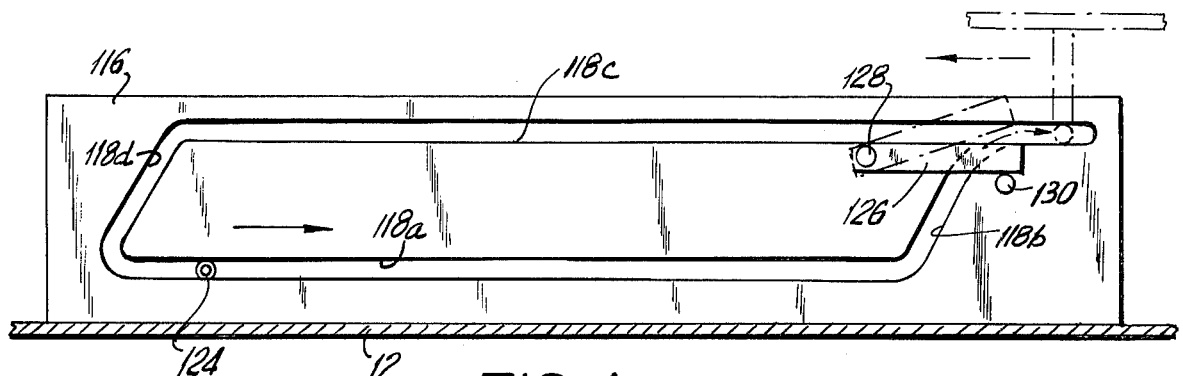
FIG. 4 is a sectional, elevational view, partially in phantom taken along line 4—4 of FIG. 3.

As shown in FIG. 4, a gate comprising a bracket 126 is pivotally mounted on the cam plate 116 by means of a pin 128. The cam follower 124 will push the bracket 126 to the phantom outlined position shown in FIG. 4 when the cam follower 124 moves from the cam track 118b to the cam track 118c. The shaft 122 guides a bracket 132 having a slot 134 therein through which the shaft 122 extends. The bracket 132 extends through a slot 136 formed in the plate 12 and terminates in a bracket 138 that slidingly rides on a shaft 140. This form of mounting arrangement prevents twisting in an angular direction, either clockwise or counter clockwise, of the bracket 120 and hence the carriage 22.

A drawer 142 having a rectangular opening 144 is provided for receiving the tray 14. The drawer 142 includes a pair of spaced apart parallel side rails 146. Frame members 148 each having a groove 150 therein are arranged to slidingly receive the rail 146 of the drawer 142.

The bracket 132 is also provided with an arm 152 from which extends a pin 154. The arm 152 is further provided with a pivotally mounted lever 156.

The loop 16 is comprised of a U-shaped oxidation resistant metal strap 200 having a pair of dimples 202 formed at the lower end thereof. A suitable material is NIKROTHAL No. 6 made by Kanthal Corporation of Bethel, Connecticut. In FIG. 3, the dimples 202 would be seen as one behind the other. The U-shaped strap 200 is secured to a support member 204 which is mounted on the shaft 112. A transverse strap 206 having a pair of contacts 208 also forms part of the loop 16. When the loop 16 reaches the right hand end of its travel as viewed in FIG. 2, the contacts 208 will engage contacts 210 that are mounted on bracket 212. The contacts 210 are electrically connected to a transformer 214 and to a relay 216 which is energized from a suitable voltage source by a control signal from a conventional solid state circuit so that when the loop 16 is at the extreme right hand position, the electrical coupling of the contacts 208 and 210 will close the circuit to sterilize loop 16.

Figure 3A:
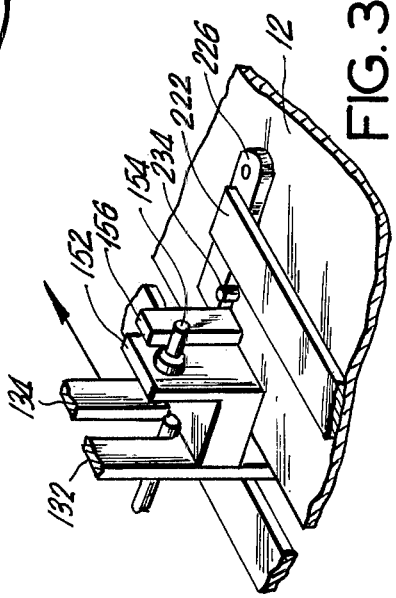
FIG. 3A is a fragmentary, perspective view of a portion of FIG. 3.

Latching and unlatching of the tray 14 is accomplished by a parallel linkage mechanism generally designed by the reference character 220 in FIG. 2. Parallel bars 222 and 224 are pivotally coupled, proximate the ends thereof, to a link 226 and a latch 228. A spring 230 biases the latch 228 which is arranged to be releasably engaged by a pin 232. It will be appreciated from FIG. 3A that the lever 156 can ride over the link 226 when the loop 16 moves to the right as in FIG. 2 but that the pin 154 prevents the lever 156 from moving in the opposite angular direction. Similarly, when the tray 14 is inserted, the pin 232 extending downwardly therefrom engages the latch 228 and displaces the parallel linkage mechanism 220 in a clockwise direction (FIG. 2) against the biasing of the spring 230 but that a stop pin 234 prevents the opposite angular displacement of the parallel linkage mechanism 220.

Figure 5:
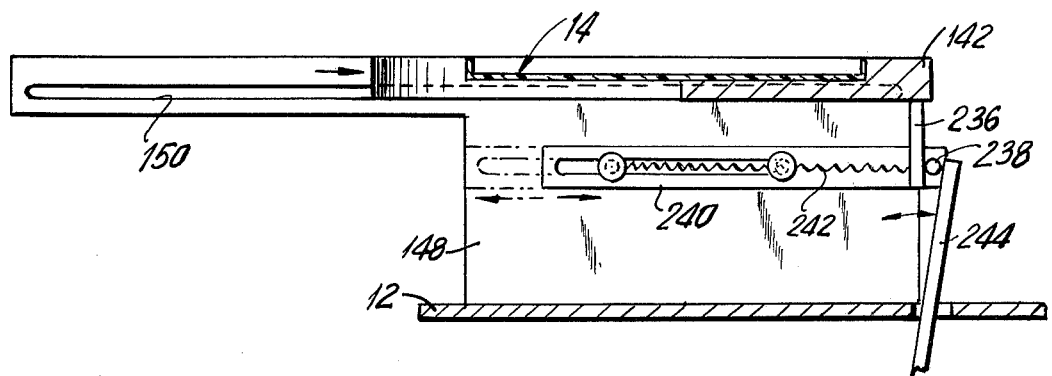
FIG. 5 is a fragmentary sectional elevational view taken along line 5—5 of FIG. 2.

When the drawer 142 is fully inserted, as shown in FIG. 2, a second pin 236 extending downwardly therefrom engages a projection 238 which is mounted on a slide 240 that is secured to the frame 148. A spring 242 biases the slide 240. Thus, when the tray 14 is inserted the spring 242 is tensioned. When the streaking cycle is over and the latch 228 is disengaged, as described above, the tray 14 will be ejected by the spring 242. Concurrent with the insertion of the tray 14 the second pin 236 and the projection 238 deflect the arm 244 (FIG. 5) of a switch (not shown) in order to close an electrical circuit and thereby energize the motors 30 and 70.

In order to provide a non-linear distribution of bacteria the traverse rate in the Y direction is changed by zones. Referring to FIG. 7B it will be seen that Zone A shows a greater number of figure eight patterns than Zone B and in turn Zone C has a lesser number than Zone B, etc.

Figure 8:
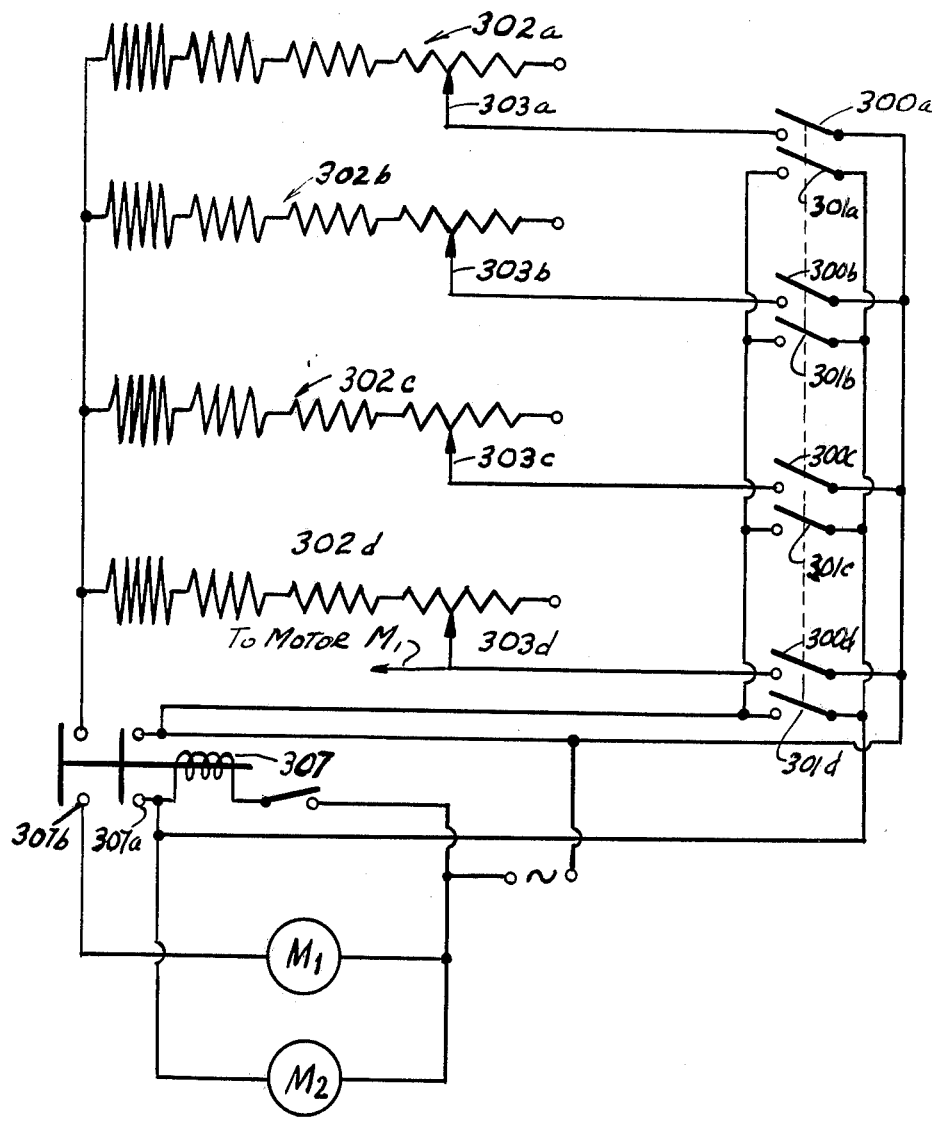

It is also desirable to provide a limited number of repeatable programs having different traverse rates. This is accomplished by controlling the speed of motor $M_1$ as the carriage moves the "loop" from zone to zone. It is within the state of the art to provide programmers to accomplish this function and accordingly by way of example and without intent to be limiting there is schematically disclosed in FIG. 8 a typical control apparatus.

Assuming four programs, the apparatus would be provided with a selection means which may include four separate panel mounted switches 300a, 300b, 300c and 300d. A second switch, 301a, 301b, 301c and 301d of the momentary contact type is ganged to each of the switches 300a, 300b, 300c and 300d respectively. Actually one of the pairs of switches 300a, 301a, etc. energizes motor 70 through contacts 307a of holding relay 307 and motor 30 through contacts 307b and a selected one of variable resistors, 302a, 302b, 302c or 302d. The resistors are shown as four section devices, each of which may be linear or non-linear so as to meet the program desired. The wipers 303a, 303b, 303c and 303d may be carried by a common shaft 304 mechanically coupled through a gear train or other linkage to the (not shown) output shaft of motor $M_1$. This establishes that the longitudinal position of the loop is related to a given zone of the variable resistor. Thus the change in resistance in the motor M circuit acts to control the speed of the motor.

As the loop is brought back to the sterilizing position a sensor 309 (FIG. 3) controls switch 310 which interrupts the current to holding relay 307 and energizes relay 216 to energize transformer 214.

Associated with motor 30 are reversing switches (not shown) which reverse the direction of rotation as the carriage reaches the end of travel in a given direction.

It is important that the pattern intersect uniformly this feature as shown in FIGS. 7A and 7B, the points of intersection being shown by dots.

As shown in FIG. 2 motor 70 should rotate counterclockwise to insure that the direction of the pattern as shown by the arrows at the outer edges be in the same longitudinal direction the loop is following.

It will be noted that the loop is provided with two dimples. This permits the forming of two figure eight loops simultaneously.

What we claim as new and desire to secure by letters Patent is:

1. Automatic bacterial specimen streaking apparatus comprising:
   a. a table;
   b. means for mounting a tray containing the specimen on said table whereby the tray is non-moveably held with respect to said table when said apparatus is in use;

c. moveable loop means positioned above said mounting means in the vicinity of the area to be occupied by the tray, said loop means being arranged to selectively contact the specimen in the tray;

d. first displacing means for moving said loop means from a starting position in a first direction over the area of said mounting means to be occupied by the tray;

e. second displacing means for moving said loop means from a starting position in a second direction over the area of said mounting means to be occupied by the tray, said second displacing means moving said loop means concurrently with the movement thereof in said first direction, said second direction being substantially perpendicular to said first direction to thereby define a figure eight movement pattern of said loop means;

f. a drive system for synchronously moving said first and said second displacing means;

g. means for advancing said loop means from the starting position thereof and in a direction parallel to said first direction of movement after the completion of each figure eight pattern to thereby define a plurality of successive figure eight patterns having a plurality of cross-over points between adjacent figure eight patterns; and h. means for returning said loop means to the starting position thereof after a predetermined length of travel in said first direction.

2. The apparatus according to claim 1 wherein said tray mounting means comprises a frame secured to said table, a drawer slidably positioned within said frame and latch means for releasably holding the tray.

3. The apparatus according to claim 2 wherein there is further included switch means responsive to the placement of the tray on said mounting means at a location below said loop means, said switch means closing a signal generating circuit for energizing said drive system.

4. The apparatus according to claim 2 wherein there is further included means for automatically releasing said latch means at the conclusion of a streaking cycle.

5. The apparatus according to claim 1 wherein said loop means comprises a strap having at least one dimple on the surface thereof that contacts the specimen.

6. The apparatus according to claim 5 wherein said loop means includes two dimples arranged parallel to said first direction of movement.

7. The apparatus according to claim 5 wherein said strap is electrically conductive.

8. The apparatus according to claim 1 wherein said first and said second displacing means are crank mechanisms and said drive system comprises a motor and a gear and belt arrangement driven by said motor, said crank mechanisms being coupled to and driven by said gear and belt arrangement.

9. The apparatus according to claim 8 wherein one of said crank mechanisms has a crank arm whose effective radius of rotation is twice as large as the radius of rotation of the crank arm of said other crank mechanism.

10. The apparatus according to claim 8 further including a plate for supporting said crank mechanisms whereby said crank mechanisms are linearly moveable in said first and second directions.

11. The apparatus according to claim 10 further including a carriage for supporting said plate, said carriage being coupled to said advancing means.

12. The apparatus according to claim 11 wherein said advancing means comprises a reversible motor and an endless chain driven by said motor, said carriage being coupled to said chain.

13. The apparatus according to claim 12 wherein said reversible motor is a variable speed motor.

14. The apparatus according to claim 1 wherein there is further included means for automatically sterilizing said loop means at the end of each streaking cycle.

15. The apparatus according to claim 1 wherein there is further included means for lifting said loop means from the surface of the specimen at the end of each streaking cycle and for returning said loop means to the starting position thereof at said elevated position.

* * * * *